United States Patent [19]

Horn et al.

[11] 4,178,317

[45] Dec. 11, 1979

[54] MANUFACTURE OF OLEFINICALLY UNSATURATED ALIPHATIC OR CYCLOALIPHATIC HYDROCARBONS

[75] Inventors: Peter Horn, Hirschberg; Otto-Alfred Grosskinsky; Hugo Fuchs, both of Ludwigshafen, all of Fed. Rep. of Germany

[73] Assignee: BASF Aktiengesellschaft, Fed. Rep. of Germany

[21] Appl. No.: 907,678

[22] Filed: May 19, 1978

[30] Foreign Application Priority Data

Jun. 10, 1977 [DE] Fed. Rep. of Germany ....... 2726106

[51] Int. Cl.$^2$ ................................................ C07C 3/00
[52] U.S. Cl. .................................... 585/357; 585/638; 585/640
[58] Field of Search .................................... 260/666 A

[56] References Cited

U.S. PATENT DOCUMENTS 4,024,171  5/1977  McArthur ....................... 260/666 A

FOREIGN PATENT DOCUMENTS 943745 12/1963 United Kingdom.

Primary Examiner—Veronica O'Keefe
Attorney, Agent, or Firm—Keil & Witherspoon

[57] ABSTRACT

Olefinically unsaturated aliphatic or cycloaliphatic hydrocarbons are manufactured by bringing alkanecarboxylic acids of 3 to 20 carbon atoms, alkanedicarboxylic acids of 4 to 20 carbon atoms or 5-membered or 6-membered cycloalkanecarboxylic acids or their alkyl, cycloalkyl, aralkyl or phenyl esters, in the gas phase, at from 250° to 800° C., into contact with catalysts in which the active composition consists of boron trioxide, boric acid and/or boron nitride, together with one or more of the oxides of aluminum, silicon, tin, lead, titanium and zirconium.

9 Claims, No Drawings

MANUFACTURE OF OLEFINICALLY UNSATURATED ALIPHATIC OR CYCLOALIPHATIC HYDROCARBONS

The present invention relates to a process for the manufacture of olefinically unsaturated aliphatic or cycloaliphatic hydrocarbons by heating alkanecarboxylic acids of 3 to 20 carbon atoms, alkanedicarboxylic acids of 4 to 20 carbon atoms or 5-membered or 6-membered cycloalkanecarboxylic acids or the alkyl, cycloalkyl, aralkyl or phenyl esters of these at from 250° to 800° C. in the gas phase in the presence of a catalyst.

There is a frequent requirement to convert carboxylic acids, obtained, for example, by oxidation processes, or to convert carboxylic acids or their esters, obtained as by-products of carbonylation processes, into the corresponding olefins by decarbonylation. The decarbonylation of carboxylic acids of their esters is of particular interest if it permits olefins which are not readily accessible to be obtained from the more easily accessible carboxylic acids or their esters.

It is true that German Published Application DAS No. 1,158,050 has disclosed that carboxylic acids can be converted into acid anhydrides and/or ketones by heating at from 250° to 800° C. in the gas phase in the presence of a catalyst comprising oxides, hydroxides and phosphates of main groups 2 to 4 and sub-groups 3 to 8 of the periodic table. However, the corresponding olefins cannot be obtained by this method.

It is an object of the present invention to provide a process by means of which carboxylic acids or their esters can be converted by decarbonylation into the corresponding olefins.

We have found that this object is achieved by a process for the manufacture of olefinically unsaturated aliphatic or cycloaliphatic hydrocarbons by heating alkanecarboxylic acids of 3 to 20 carbon atoms, alkanedicarboxylic acids of 4 to 20 carbon atoms or 5-membered or 6-membered cycloalkanecarboxylic acids or their alkyl, cycloalkyl, aralkyl or phenyl esters at from 250° to 800° C. in the gas phase in the presence of a catalyst whereof the active composition consists of baron trioxide, boric acid and/or boron nitride together with one or more of the oxides of aluminum, silicon, tin, lead, titanium or zirconium.

The new process has the advantage that carboxylic acids or their esters can be converted in a simple manner into olefins. It has the further advantage that it is easily scaled up to industrial operation and runs with good yields and good conversions.

It is preferred to start from an alkanecarboxylic acid of 3 to 16 carbon atoms, an alkanedicarboxylic acid of 4 to 12 carbon atoms or cyclohexanecarboxylic acid. Their alkyl, cycloalkyl, aralkyl and phenyl esters, especially their alkyl esters, where alkyl is of 1 to 8 carbon atoms, their cyclohexyl esters, their benzyl esters and their phenyl esters, are also suitable. The use of the free carboxylic acids or of the corresponding methyl esters as starting materials is preferred. The new process is of particular industrial importance for the manufacture of cyclohexene from hexahydrobenzoic acid or its esters. Specific examples of suitable starting materials are propionic acid, methyl propionate, isobutyric acid, butyl isobutyrate, caproic acid, methyl caproate, decanecarboxylic acid, palmitic acid, methyl palmitate, dimethyl adipate, dimethyl methylglutarate, methyl cyclopentanecarboxylate, hexahydrobenzoic acid, methyl hexahydrobenzoate, cyclohexyl hexahydrobenzoate, phenyl hexahydrobenzoate and benzyl hexahydrobenzoate.

Of course the decarbonylation of monocarboxylic acids or their esters gives monoolefinically unsaturated compounds with one carbon atom fewer, whilst the decarbonylation of dicarboxylic acids gives diolefins with 2 carbon atoms fewer.

The reaction is carried out in the gas phase. Advantageously, the carboxylic acids or their esters, used as starting materials, are vaporized, but inert gases, such as nitrogen, noble gases, carbon dioxide, carbon monoxide, steam or flue gases may additionally be employed in order to facilitate using the starting materials in the gas phase. The amount of such inert gas used is not critical, since the gas merely serves as a carrier gas.

The reaction is advantageously carried out under atmospheric pressure, slightly superatmospheric pressure, or reduced pressure, for example down to 20 mm Hg. A pressure range from atmospheric pressure to 100 mm Hg has proved particularly suitable.

The reaction takes place at from 250° to 800° C., advantageously from 250° to 700° C.

The reaction is carried out in the presence of catalysts, of which the active composition consists of boron trioxide, boric acid and/or boron nitride, together with one or more of the oxides of aluminum, silicon, lead, titanium or zirconium. Preferred active compositions contain from 10 to 60, especially from 20 to 55, % by weight of boron trioxide, boric acid and/or boron nitride. The remainder of the active composition then consists of one of the above oxides. Active compositions which contain boron trioxide or boric acid, especially the former, have proved particularly suitable.

The preferred oxides also present in the active compositions include alumina, e.g. in the form of hydrargillite, boehmite or bayerite and their dehydration products, e.g. $\gamma$-, $\epsilon$- or $\delta$-alumina, as well as tin dioxide, titanium dioxide and silica gel. The use of alumina, or of titanium dioxide in the anatase modification, is preferred. $\alpha$-Alumina is industrially of particular importance since it reduces the isomerization of the olefinically unsaturated hydrocarbons formed.

Further catalysts according to the invention are those resulting from mixed phase formation between one of the boron compounds used and the oxides mentioned above, e.g. boron trioxide and alumina, giving compounds of the empirical formula $9\,Al_2O_3 \cdot 2\,B_2O_3$ or $2\,Al_2O_3 \cdot B_2O_3$. In such mixed phases, alumina is no longer detectable by X-ray crystallography.

Advantageously, the active compositions additionally contain one or more of the elements of group VIII of the periodic table, manganese, chromium, copper, zinc, cadmium, silver and/or gold. The said elements are preferably present in the active composition in an amount of from 0.1 to 10% by weight (calculated as metal), based on the active composition.

Suitable catalysts are prepared by, for example, mixing alumina and boron oxide or boric acid, or compounds which form these on heating, e.g. ammonium borate, with or without the addition of compounds of the above heavy metals, e.g. manganese nitrate, manganese acetate, cobalt nitrate, cobalt acetate, nickel nitrate, rhodium chloride, tris-(triphenylphosphine)-rhodium chloride, iridium chloride, palladium nitrate, platinum chloride, zinc nitrate, cadmium nitrate, copper nitrate, silver nitrate or gold chloride, if appropriate working the mixture into a paste with water and kneading the paste, and molding the material into shapes, e.g. pills, tablets or extrudates. Advantageously, the material is then dried and heated at up to 400° C. If the active composition is to be used as a fluidized bed catalyst, it is advisable to comminute the moldings to the desired size, e.g. to an average particle size of from 0.01 to 2 mm, especially from 0.2 to 1 mm. The catalyst composition is then heated at from 600° to 1,500° C., preferably from 700° to 1,300° C. and especially from 1,000° to 1,200° C. for a period of from 15 minutes to 20 hours, especially from 30 minutes to 5 hours.

In another advantageous embodiment, the active compositions according to the invention are obtained by impregnating, for example, alumina or one of the other oxides mentioned, which already have a particle size of from 0.1 to 2 mm, with boron trioxide or boron compounds which under the conditions of manufacture of the catalyst are converted into boron trioxide or boric acid, at an elevated temperature, under pressure, in the presence of a solvating agent. Suitable materials, in addition to boron trioxide and boric acid, are boron trichloride, boron trifluoride and ammonium borate. An advantageous solvating agent is water, with or without the addition of small amounts of ammonia or mineral acids, e.g. hydrochloric acid or perchloric acid; other suitable solvating agents are alcohols, e.g. methanol, ethanol and glycerol. Advantageously, the oxides are impregnated under superatomspheric pressure, e.g. at from 1.1 to 20 bars, at an elevated temperature, e.g. at from 50° to 250° C. The weight ratio of solvent to starting materials used is advantageously from 1:1 to 10:1. In particular, equal parts by weight of solvent and starting materials are used. Such an impregnated catalyst is then dried at from 50° to 200° C. and subsequently heated at from 600° to 1,500° C. The catalysts may be used unsupported or on carriers.

The catalysts may be used as a fixed bed, but are preferably used in a fluidized bed, in which they undergo a rising and falling movement. Residence times of from 0.01 to 50 seconds over the catalyst have proved advantageous for the reaction.

By way of example, the process may be carried out by fluidizing a finely divided supported catalyst, for example aluminum oxide containing boron trioxide, in an apparatus suitable for producing a fluidized bed, heating the catalyst to the stated temperature and passing the carboxylic acid ester or carboxylic acid in the gaseous form, with or without a carrier gas, through the catalyst bed from below. Of course, it is also possible to pass the liquid carboxylic acid or liquid ester into the heated catalyst bed. The gas mixture obtained is cooled and in doing so the olefins, unconverted starting materials and, when using esters, the corresponding alcohols, are condensed out. The inert gaseous constituents can be re-used as the carrier gas. Equally, unconverted starting materials can be recycled to the reaction. It may or may not be necessary to separate the olefins formed from the alcohol by-products, for example by distillation.

Olefinically unsaturated hydrocarbons manufactured by the process of the invention may be used, for example, to manufacture aldehydes by the oxo reaction. Cyclohexene obtained by the process of the invention may be used for the manufacture of cyclohexanol, for example as described in British Pat. No. 339,592.

The Examples which follow illustrate the process of the invention.

EXAMPLE 1

200 g of hexahydrobenzoic acid per hour were passed from a vaporizer into a fluidized bed reactor at 550° C., the reactor being charged with 630 g of a catalyst which consisted of 52.3 percent by weight of $\gamma$-$Al_2O_3$ and 45.5 percent by weight of $B_2O_3$, and had a particle size of from 0.1 to 0.3 mm and a bulk density of 0.63 kg per liter. The catalyst was fluidized by means of the hexahydrobenzoic acid vapor and a slight stream of nitrogen, as well as by maintaining a reduced pressure of 360 mm Hg. The resulting reaction vapors were condensed. The following products were isolated after 3 hours' operation: 86 g of water and 384 g of an organic phase. The organic phase was washed with aqueous sodium bicarbonate solution in order to remove traces of unconverted hexahydrobenzoic acid and was then distilled. Examination of the distillate by gas chromatography showed the following composition: 63% by weight of cyclohexene, 29% by weight of 1-methylcyclopent-1-ene, 4% by weight of 3-methylcyclopent-1-ene and 4% by weight of 4-methylcyclopent-1-ene.

EXAMPLE 2

The procedure followed was as described in Example 1 except that before use the catalyst employed in Example 1 was heated for 4 hours at 1,150° C. After 7 hours' operation, 61 g of water and 356 g of an organic phase, consisting, after working up as described in Example 1, of 72% by weight of cyclohexene and 23% by weight of 1-methylcyclopent-1-ene, were obtained.

EXAMPLE 3

The procedure followed was as described in Example 1, except that the catalyst additionally contained 1.3% by weight of rhodium. After 3 hours' operation, 69 g of water and 366 g of an organic phase, consisting, after working up as described in Example 1, of 74% by weight of cyclohexene, 19.6% by weight of 1-methyl-1-cyclopent-1-ene and 5.5% by weight of benzene, were obtained.

EXAMPLE 4

300 g of hexahydrobenzoic acid per hour were passed from a vaporizer into a fluidized bed reactor at the reaction temperature of 480° C., the reactor being charged with 795 g of a catalyst which consisted of 35 percent by weight of $\gamma$-$Al_2O_3$, 45 percent by weight of $B_2O_3$ and 20 percent by weight of $SnO_2$, and had a particle size of from 0.1 to 0.3 mm and a bulk density of 0.795 kg per liter. The catalyst was fluidized by means of the hexahydrobenzoic acid vapor and a slight stream of nitrogen, as well as by maintaining a reduced pressure of 360 mm Hg. The resulting reaction vapors were condensed. After 4 hours' operation, 186 g of water and 813 g of an organic phase consisting, after working up as described in Example 1, of 68.3% by weight of cyclohexene and 19.2% by weight of 1-methyl-cyclopent-1-ene, were isolated.

EXAMPLE 5

200 g of methyl hexahydrobenzoate per hour were passed from a vaporizer into a fluidized bed reactor at the reaction temperature of 550° C., the reactor being charged with 630 g of a catalyst which consisted of 52.3 percent by weight of $\gamma$-$Al_2O_3$ and 45.5 percent by weight of $B_2O_3$, and had a particle size of from 0.1 to 0.3 mm and a bulk density of 0.63 kg per liter. The catalyst was fluidized by means of the methyl hexahydrobenzoate vapor and a slight stream of nitrogen, as well as by maintaining a reduced pressure of 360 mm Hg. The resulting reaction vapors were condensed. After 3 hours' operation of the installation, 184 g of an organic phase, consisting, after washing with water and distillation, of 82.3% by weight of cyclohexene and 17.7% by weight of 1-methylcyclopent-1-ene, were isolated.

EXAMPLE 6

The procedure followed was as described in Example 3 except that the reaction temperature was 700° C. After 3 hours' operation of the installation, 265 g of an organic phase consisting, after washing with water and distillation, of 74% by weight of cyclohexene and 25% by weight of 1-methyl-cyclopent-1-ene, were isolated.

EXAMPLE 7

200 g of cyclohexyl hexahydrobenzoate per hour were passed from a vaporizer into a fluidized bed reactor at the reaction temperature of 600° C., the reactor being charged with 630 g of a catalyst which consisted of 52.3 per cent by weight of $\gamma$-$Al_2O_3$ and 45.5 percent by weight of $B_2O_3$, and had a particle size of from 0.1 to 0.3 mm and a bulk density of 0.63 kg per liter. The catalyst was fluidized by means of the cyclohexyl hexahydrobenzoate vapor and a slight stream of nitrogen, as well as by maintaining a reduced pressure of 360 mm Hg. The resulting reaction vapors were condensed. After 3 hours' operation of the installation, 440 g of an organic phase were obtained, which, after washing with water and distillation, consisted of 54% by weight of 1-methylcyclopent-1-ene and 42.6% by weight of cyclohexene.

EXAMPLE 8

The procedure followed was as described in Example 4, except that phenyl hexahydrobenzoate was used as the ester and that the reaction temperature was 700° C. After 3 hours' operation of the installation, 243 g of phenol and 266 g of an organic phase consisting, after washing with water and distillation, of 62% by weight of 1-methylcyclopent-1-ene and 32% by weight of cyclohexene, were isolated.

EXAMPLE 9

The procedure followed was as described in Example 4, except that the ester employed was benzyl hexahydrobenzoate and the reaction temperature was 700° C. After 3 hours' operation, 77 g of toluene, 31 g of benzaldehyde, 51 g of benzyl alcohol and 122 g of an organic phase consisting, after washing with water and distillation, of 44% by weight of 1-methylcyclopent-1-ene and 36% by weight of cyclohexene, were isolated.

EXAMPLE 10

200 g of caproic acid per hour were passed from a vaporizer into a fluidized bed reactor at the reaction temperature of 550° C., the reactor being charged with 630 g of a catalyst which consisted of 50% by weight of $B_2O_3$ and 50% by weight of $\gamma$-$Al_2O_3$, and had a particle size of from 0.1 to 0.3 mm and a bulk density of 0.63 g per liter. The catalyst was fluidized by means of the caproic acid vapor and a slight stream of nitrogen, as well as by maintaining a reduced pressure of 360 mm Hg. The resulting reaction vapors were condensed. After 3 hours' operation of the installation, 229 g of an organic phase consisting of 1.5% by weight of 3-methylbut-1-ene, 14.3% by weight of pent-1-ene, 10% by weight of 2-methylbut-1-ene, 30% by weight of trans-pent-2-ene, 17.2% by weight of cis-pent-2-ene and 21% by weight of 2-methylbut-2-ene were isolated.

We claim:

1. A process for the manufacture of olefinically unsaturated aliphatic or cycloaliphatic hydrocarbons which comprises:
    contacting at least one member of the group consisting of (a) alkanecarboxylic acids of 3 to 20 carbon atoms, (b) 5-membered or 6-membered cycloalkanecarboxylic acids and (c) alkyl, cycloalkyl, aralkyl or phenyl esters of (a) or (b),
    in the gas phase,
    at a temperature of from about 250° to 800° C.,
    with a catalyst in which the active material is a combination of a compound selected from the group consisting of boron trioxide, boric acid and boron nitride and a compound selected from the group consisting of aluminum oxide, silicon dioxide, titanium dioxide and zirconium dioxide.
2. The process of claim 1, wherein the temperature is maintained at from 250° to 700° C.
3. The process of claim 1, wherein the catalyst contains from 10 to 60% by weight of boron trioxide, boric acid and/or boron nitride, based on the active composition.
4. The process of claim 1, wherein boron trioxide is used.
5. The process of claim 1, wherein the active composition additionally contains one or more of the elements of group VIII of the periodic table, manganese, chromium, copper, zinc, cadmium, silver or gold.
6. The process of claim 1, wherein alumina is used.
7. The process of claim 1, wherein $\alpha$-alumina is used.
8. The process of claim 1, wherein hexahydrobenzoic acid or one of its alkyl, cycloalkyl, aralkyl or phenyl esters is used as the starting material.
9. The process of claim 1, wherein the catalyst corresponds to the composition 9 $Al_2O_3$ . 2 $B_2O_3$ or 2 $Al_2O_3$ . $B_2O_3$.

* * * * *